United States Patent
Hippe et al.

(10) Patent No.: US 10,143,646 B2
(45) Date of Patent: *Dec. 4, 2018

(54) OXIDATIVE COLORING OR BLONDING AGENT GENTLE ON HAIR, AND GENTLE HAIR COLORING OR BLONDING METHOD

(71) Applicant: Henkel AG & Co. KGsA, Duesseldorf (DE)

(72) Inventors: Thomas Hippe, Appen (DE); Astrid Kleen-Fehres, Hamburg (DE); Hartmut Manneck, Barnitz (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/247,719

(22) Filed: Aug. 25, 2016

(65) Prior Publication Data

US 2017/0079901 A1   Mar. 23, 2017

(30) Foreign Application Priority Data

Sep. 21, 2015   (DE) .......................... 10 2015 218 077

(51) Int. Cl.
| | | |
|---|---|---|
| *A61Q 5/10* | (2006.01) | |
| *A61K 8/84* | (2006.01) | |
| *A45D 7/02* | (2006.01) | |
| *A61K 8/22* | (2006.01) | |
| *A61K 8/44* | (2006.01) | |
| *A61K 8/73* | (2006.01) | |
| *A45D 7/00* | (2006.01) | |

(52) U.S. Cl.
CPC ................. *A61K 8/84* (2013.01); *A45D 7/02* (2013.01); *A61K 8/22* (2013.01); *A61K 8/447* (2013.01); *A61K 8/731* (2013.01); *A45D 2007/001* (2013.01)

(58) Field of Classification Search
CPC ...... A45D 7/02; A45D 2007/001; A61K 8/84; A61K 8/447; A61K 8/731; A61K 8/22; A61K 2800/884; A61Q 5/10
See application file for complete search history.

(56) References Cited

U.S. PATENT DOCUMENTS

| | | | |
|---|---|---|---|
| 5,030,241 A * | 7/1991 | Clausen ................. | A61K 8/418 564/441 |
| 2006/0248662 A1* | 11/2006 | Legrand .................. | A61K 8/36 8/405 |
| 2011/0158925 A1* | 6/2011 | Ascione .................. | A61K 8/22 424/62 |
| 2015/0053228 A1* | 2/2015 | Bonauer ............ | A45D 19/0008 132/208 |

FOREIGN PATENT DOCUMENTS

CA         2066226 A1      3/1991

OTHER PUBLICATIONS

English Abstract (May 24, 2017) of the Japanese Patent No. 2006273782 A1.*
STIC Search Report dated Mar. 22, 2017.*

* cited by examiner

*Primary Examiner* — Eisa B Elhilo
(74) *Attorney, Agent, or Firm* — P. Scott Smith

(57) ABSTRACT

The present invention relates to an agent for oxidatively coloring or blonding hair that is gentle on the hair, and to a gentle method for oxidatively coloring or blonding hair, in which keratin fibers are protected from oxidative influences.

13 Claims, No Drawings

OXIDATIVE COLORING OR BLONDING AGENT GENTLE ON HAIR, AND GENTLE HAIR COLORING OR BLONDING METHOD

FIELD OF THE INVENTION

The present invention generally relates to an agent for oxidatively coloring or blonding hair that is gentle on the hair, and to a gentle method for oxidatively coloring or blonding hair, in which keratin fibers are protected from oxidative influences and/or oxidative damage to the hair is repaired.

BACKGROUND OF THE INVENTION

The problem with oxidatively coloring or blonding hair is that the keratin fibers may be damaged by the aggressive substances. In particular, the natural hydrophobicity of the keratin fiber is reduced since the coloring or lightening agents initially have to render the hair penetrable so as to develop their effect. The water-repelling action, however, provides natural protection of the hair, and additionally is closely associated with parameters desired by the consumer, such as shine, suppleness, feel, and "laying" of the hair.

So as to overcome the aforementioned drawbacks, what are known as pre-treatment agents are available on the market, which are to protect the hair from aggressive influence. However, these often weigh the hair down or impair the success of the subsequent lightening process or coloration of the hair, and in particular the washing fastness of the color may be adversely affected by the pre-treatment agent. In addition, numerous post-treatment agents are known, which are used to attempt to repair damage caused to the hair during the oxidative coloring treatment. All of these methods, however, require a multi-stage application process, involving an application of a further hair treatment agent prior to or after coloring. This is frequently perceived as inconvenient by the consumer, since the oxidative coloring treatment itself already involves multiple work steps and an exposure time of as much as 60 minutes, making the process very complex.

It was the object of the present invention to provide an agent and a method for oxidatively coloring hair using a treatment that protects hair, which overcomes the aforementioned drawbacks, without negatively influencing the color result of the oxidative coloring treatment. In particular, a coloring agent and a method were to be provided, in which the hair is not weighed down and which cause preferably little damage to the hair. Furthermore, the achieved protection of the hair should command as little time as possible and preferably take place directly together with the coloring step.

The use of permanently cationic polymers in hair care is state of the art. These are widely used in shampoos, and in particular in conditioners, so as to develop nourishing effects there. Patent application CA 2066226 A, for example, discloses hair conditioners comprising amphoteric polymers composed of cationic and anionic units, wherein the cationic units are present in excess in relation to the anionic units, and the polymers are thus, in sum, permanently cationic.

It was now found that oxidative coloring agents that, in addition to typical components such as water, ammonium hydroxide and/or monoethanolamine serving as the alkalizing agent, and a peroxide compound such as hydrogen peroxide, comprise a special combination composed of a select polymer, a permanently cationic polymer and at least one amino acid, result in considerably improved protection of the hair during the oxidative coloring treatment, without impairing the results of the oxidative coloring treatment. Surprisingly, it was found that the combination according to the invention, composed of a select polymer, a permanently cationic polymer and at least one amino acid, protects the hair during coloring and/or lightening from damage caused by the high pH of the agent and by the oxidizing agent. This was able to be established, among other things, in that less hair breakage occurred during subsequent combing, and the hair lost less elasticity, as demonstrated by stress-strain measurements, than after the application of coloring and blonding agents not according to the invention.

Furthermore, other desirable features and characteristics of the present invention will become apparent from the subsequent detailed description of the invention and the appended claims, taken in conjunction with this background of the invention.

BRIEF SUMMARY OF THE INVENTION

An oxidative coloring or blonding agent for keratin fibers, in particular for human hair, comprising: at least one polymer A, which includes at least ten constitutional units of formula (I),

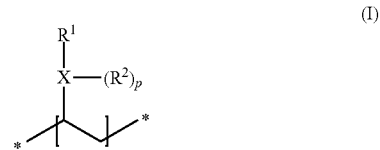

where X denotes nitrogen or oxygen, and $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, which are preferably selected from N and O, and/or optionally is substituted with at least one C1 to C6 alkyl group and/or with at least one functional group, and p=0 when X denotes oxygen, and p=1 when X denotes nitrogen; furthermore comprising at least one permanently cationic polymer; furthermore at least one amino acid; furthermore at least one alkalizing agent, selected from ammonium hydroxide, monoethanolamine and sodium silicates, and mixtures thereof; optionally at least one oxidation dye precursor and/or at least one direct dye; water; and at least one peroxide compound.

A method for oxidatively coloring and/or lightening keratin fibers, and in particular human hair, comprising the following method steps: providing a composition (A), comprising at least one polymer, which includes at least ten constitutional units of formula (I),

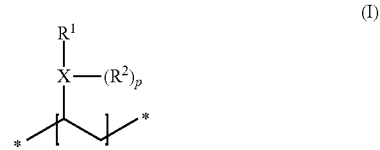

where X denotes nitrogen or oxygen, and $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, which are preferably selected from N and O, and/or optionally is substituted with at least one C1 to C6 alkyl group and/or with at least one functional group, and p=0 when X denotes oxygen, and p=1 when X denotes nitrogen, furthermore comprising at least one permanently cationic polymer, furthermore at least one amino acid, and water; providing a composition (B), comprising at least one alkalizing agent, selected from ammonium hydroxide, monoethanolamine and sodium silicates, and mixtures thereof, water, and optionally at least one oxidation dye precursor and/or at least one direct dye; providing a composition (C), comprising at least one peroxide compound, which preferably is hydrogen peroxide; mixing compositions (A), (B) and (C) with each other, immediately thereafter; applying the mixture of (A), (B) and (C) to the keratin fibers, and in particular to the human hair; rinsing after an exposure time of 1 to 60 minutes; and optionally further heat treatments, such as styling, conditioning and/or drying.

A method for oxidatively coloring and/or lightening keratin fibers, and in particular human hair, comprising the following method steps: providing a composition (AB), comprising at least one polymer, which includes at least ten constitutional units of formula (I),

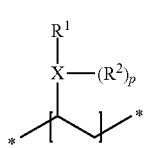

(I)

where X denotes nitrogen or oxygen, and $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, which are preferably selected from N and O, and/or optionally is substituted with at least one C1 to C6 alkyl group and/or with at least one functional group, and p=0 when X denotes oxygen, and p=1 when X denotes nitrogen, furthermore comprising at least one permanently cationic polymer, furthermore at least one amino acid, at least one alkalizing agent, selected from ammonium hydroxide, monoethanolamine and sodium silicates, and mixtures thereof, water, and optionally at least one oxidation dye precursor and/or at least one direct dye; providing a composition (C), comprising at least one peroxide compound, which preferably is hydrogen peroxide; mixing compositions (AB) and (C) with each other, immediately thereafter; applying the mixture of (AB) and (C) to the keratin fibers, and in particular to the human hair; rinsing after an exposure time of 1 to 60 minutes; and optionally further heat treatments, such as styling, conditioning and/or drying.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

In a first embodiment, the subject matter of the present invention is an oxidative coloring or blonding agent for keratin fibers, and in particular for human air, comprising:
a) at least one polymer A, which includes at least ten constitutional units of formula (I),

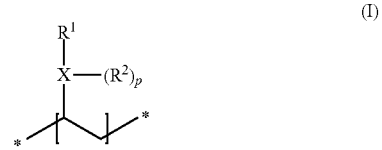

where
X denotes nitrogen or oxygen, and
$R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, which are preferably selected from N and O, and/or optionally is substituted with at least one C1 to C6 alkyl group and/or with at least one functional group, and
p=0 when X denotes oxygen, and p=1 when X denotes nitrogen, wherein the polymer does not include any permanently ionic constitutional units,
b) further comprising at least one permanently cationic polymer B,
c) furthermore at least one amino acid,
d) furthermore at least one alkalizing agent, selected from ammonium hydroxide, monoethanolamine and sodium silicates, and mixtures thereof,
e) optionally at least one oxidation dye precursor and/or at least one direct dye,
f) water, and
g) at least one peroxide compound.

Polymer A Including at Least 10 Constitutional Units of Formula (I)

The oxidative coloring or blonding agents according to the invention comprise at least one polymer A, which includes at least ten constitutional units of formula (I),

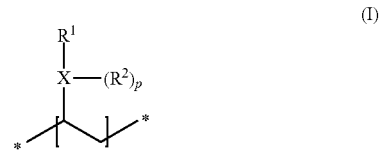

where
X denotes nitrogen or oxygen, and
$R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, which are preferably selected from N and O, and/or optionally is substituted with at least one C1 to C6 alkyl group and/or with at least one functional group, and
p=0 when X denotes oxygen, and p=1 when X denotes nitrogen,
wherein the polymer A does not include any permanently ionic constitutional units.

Surprisingly, it was found that a polymer A, as described above and addressed in greater detail hereafter, excellently enhances the protective and repair action of the combination, composed of the permanently cationic polymer B and amino acid(s), on oxidatively colored or blonded keratin fibers.

The term "polymer" within the meaning of the present invention shall be understood to cover polymers as per the IUPAC definition that include at least 10 identical constitutional units.

According to Römpp Chemie Lexikon (chemistry encyclopedia), edition of July 2009, a polymer under the definition according to the IUPAC refers to a substance that is composed of a plurality of chemically uniformly structured macromolecules (polymer molecules), wherein the macromolecules or polymer molecules differ from one another in terms of the degree of polymerization, molecular mass, and chain length. In these so-called polymer uniform substances, all macromolecules thus have an identical structure and differ only in terms of the chain length (degree of polymerization) thereof. Based on this IUPAC definition, a polymer is furthermore "a substance of a polymerization reaction which is composed of a plurality of molecules characterized by the multiple repetition of one or more species of atoms or groups of atoms (known as constitutional units, basic building blocks or repeating units) linked to each other.

The degree of polymerization denotes the number of constitutional units in a polymer. Preferred polymers A according to the invention and polymers B each have a degree of polymerization in the range of 40 to 1000, preferably 100 to 800, and particularly preferably 350 to 650. Further preferred polymers A according to the invention including at least ten constitutional units of formula (I) comprise 40 to 1000, preferably 100 to 800, and particularly preferably 350 to 650 identical constitutional units of formula (I).

$R^1$ and $R^2$, each independently of one another, preferably denote hydrogen or a $C_2$ to $C_{10}$ acyl group, which is preferably selected from an acetyl group, a propanoyl group, or an n-butanoyl group, and particularly preferably is selected from an acetyl group.

Preferred polymers A according to the invention include at least 10 constitutional units of formula (I), in which X denotes nitrogen, wherein the polymer A does not include any permanently ionic constitutional units.

Further particularly preferred polymers A according to the invention include at least 10 constitutional units of formula (I), in which X denotes nitrogen, and $R^1$ and $R^2$, together with X, form a five-membered or six-membered, saturated or unsaturated ring, which optionally includes further heteroatoms, which are preferably selected from N and O, and/or optionally is substituted with at least one C1 to C6 alkyl group and/or with at least one functional group.

When $R^1$ and $R^2$, together with X, form a five-membered or six-membered, saturated or unsaturated ring, which optionally includes further heteroatoms, which are preferably selected from N and O, then this ring is preferably substituted with at least one functional group that is selected from =O. A particularly preferred substituent combination X, $R^1$, $R^2$ is a pyrrolidone group, so that a constitutional unit of formula (I) that is particularly preferred according to the invention is a unit of formula (Ia),

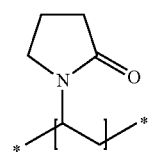

(Ia)

in which X denotes nitrogen, and $R^1$ and $R^2$, together with this nitrogen atom, form a five-membered saturated ring, which includes no further heteroatoms and is substituted at the 2-position with a functional group =O.

A further particularly preferred substituent combination X, $R^1$, $R^2$ is a ε-caprolactam group, so that a constitutional unit of formula (I) that is particularly preferred according to the invention is a unit of formula (Ib),

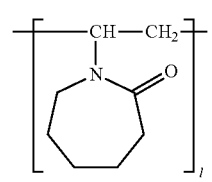

(Ib)

in which X denotes nitrogen, and $R^1$ and $R^2$, together with this nitrogen atom, form a six-membered saturated ring, which includes no further heteroatoms and is substituted with a functional group =O.

A further particularly preferred substituent combination X, $R^1$, $R^2$ is an imidazole group, so that a further unit of formula (I) that is particularly preferred according to the invention is a unit in which X denotes nitrogen, and $R^1$ and $R^2$, together with this nitrogen atom, form a five-membered unsaturated ring, which includes nitrogen as a further heteroatom.

Further preferred polymers A according to the invention comprise 25 to 100 mol %, preferably 55 to 100 mol %, and particularly preferably 85 to 100 mol % of constitutional units of formula (I), in which X denotes nitrogen, wherein the polymer A does not include any permanently ionic constitutional units.

Further preferred polymers A according to the invention comprise 25 to 100 mol %, preferably 55 to 100 mol %, and particularly preferably 85 to 100 mol % of constitutional units of formula (I), in which X denotes nitrogen, and $R^1$ and $R^2$, together with X, form a five-membered or six-membered, saturated or unsaturated ring, which optionally includes further heteroatoms, which are selected from N and O, and optionally is substituted with at least one C1 to C6 alkyl group and/or with at least one functional group, wherein the polymer A does not include any permanently ionic constitutional units.

Polymers A that are particularly preferred according to the invention comprise 98 to 100 mol % of constitutional units of formula (Ia), wherein the polymer A does not include any permanently ionic constitutional units.

Polymers A that are exceptionally preferred according to the invention comprise 98 to 100 mol % of constitutional units of formula (Ia) and have a degree of polymerization in the range of 40 to 1000, preferably 100 to 800, and particularly preferably 350 to 650, wherein the polymer A does not include any permanently ionic constitutional units. Particularly preferred polymers A are polyvinylpyrrolidone homopolymers having a degree of polymerization in the range of 40 to 1000, preferably 100 to 800, and particularly preferably 350 to 650.

A further particularly preferred substituent combination X, $R^1$, $R^2$ is a constitutional unit of formula (I), in which X denotes oxygen, p is zero, and $R^1$ denotes hydrogen.

A further particularly preferred substituent combination X, $R^1$, $R^2$ is a constitutional unit of formula (I), in which X denotes oxygen, p is zero, and $R^1$ denotes an acetyl group.

Further polymers A that are preferred according to the invention comprise 75 to 92 mol % of constitutional units of formula (I), in which X denotes oxygen, p is zero, and $R^1$ denotes hydrogen, and 8 to 25 mol % of constitutional units of formula (I), in which X denotes oxygen, p is zero and $R^1$ denotes an acetyl group, wherein the polymer A does not include any permanently ionic constitutional units.

Further polymers A that are preferred according to the invention comprise 40 to 1000, preferably 100 to 800, and particularly preferably 350 to 650 constitutional units of formula (I), 75 to 92 mol % thereof being constitutional units of formula (I), in which X denotes oxygen, p is zero, and $R^1$ denotes hydrogen, and 8 to 25 mol % of constitutional units of formula (I), in which X denotes oxygen, p is zero and $R^1$ denotes an acetyl group, wherein the polymer A does not include any permanently ionic constitutional units.

Further polymers A that are preferred according to the invention comprise 65 to 25 mol % of constitutional units of formula (Ia), and 35 to 75 mol % of constitutional units of formula (I), in which X denotes oxygen, p is zero and $R^1$ denotes an acetyl group, wherein the polymer A does not include any permanently ionic constitutional units.

Further polymers A that are preferred according to the invention comprise 40 to 1000, preferably 100 to 800, and particularly preferably 350 to 650 constitutional units of formula (I), 65 to 25 mol % thereof being constitutional units of formula (Ia), and 35 to 75 mol % of constitutional units of formula (I), in which X denotes oxygen, p is zero and $R^1$ denotes an acetyl group, wherein the polymer A does not include any permanently ionic constitutional units.

The at least one polymer A including at least ten constitutional units of formula (I) does not have any permanently ionic charges. However, it is possible for the constitutional units of formula (I) to be present in ionic, and in particular in cationic, form, for example as a result of protonation of the nitrogen atom in an acid carrier. These charges, however, are not permanent, but temporary, since they are dependent on the surrounding medium.

Preferred coloring or blonding agents according to the invention comprise the at least one polymer A including at least ten constitutional units of formula (I) in a total amount of 0.4 to 5 wt. %, preferably 0.9 to 3 wt. %, and particularly preferably 1.5 to 2.3 wt. %, in each case based on the weight of the coloring or blonding agent.

Permanently Cationic Polymer B

In addition to the at least one polymer A including at least ten constitutional units of formula (I), the coloring or blonding agents according to the invention comprise at least one permanently cationic polymer B.

In addition to at least one permanently cationically charged monomer type, the permanent cationic polymer preferably also comprises at least one permanently anionically charged monomer type, wherein the cationic monomers are present in a molar excess in relation to the anionic monomers so that the at least one second polymer according to the invention has a cationic net charge. Such polymers that are preferred according to the invention are also referred to as amphoteric or zwitterionic polymers.

In a first preferred embodiment, the coloring or blonding agents according to the invention comprise at least one permanently cationic polymer, which is selected from cationic polymers composed of monomers with quaternary ammonium groups of the general formula (IIa)

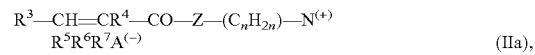

(IIa), in which $R^3$ and $R^4$, independently of one another, denote hydrogen or a methyl group, $R^5$, $R^6$ and $R^7$, independently of one another, denote an alkyl group having 1 to 4 carbon atoms, Z denotes an NH group or an oxygen atom, n denotes an integer from 2 to 4, and $A^{(-)}$ represents the anion of an inorganic or organic acid, preferably selected from cationic polymers composed of acrylamidopropyltrimethylammonium chloride, particularly preferably selected from amphoteric polymers having a cationic net charged, which by way of polymerization are composed of a) cationic monomers with quaternary ammonium groups of the general formula (IIa),

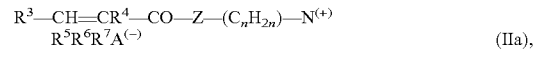

(IIa), in which $R^3$ and $R^4$, independently of one another, denote hydrogen or a methyl group, $R^5$, $R^6$ and $R^7$, independently of one another, denote an alkyl group having 1 to 4 carbon atoms, Z denotes an NH group or an oxygen atom, n denotes an integer from 2 to 4, and $A^{(-)}$ represents the anion of an inorganic or organic acid, and b) at least one unsaturated carboxylic acid, selected from acrylic acid, methacrylic acid, and crotonic acid, and mixtures of these acids, wherein the at least one unsaturated carboxylic acid may be present in the form of the salts thereof, wherein the cationic monomers are present in the polymer in a molar excess in relation to the anionic monomers, exceptionally preferably selected from amphoteric polymers having a cationic net charge, which comprise the at least one monomer type of the general formula (IIa) and the at least one monomer type of the unsaturated carboxylic acid, selected from acrylic acid, methacrylic acid and crotonic acid, and mixtures thereof, in a molar ratio from 60:40 to 95:5, and preferably from 75:25 to 90:10 in relation to each other, exceptionally preferably selected from amphoteric copolymers having a cationic net charge, which are composed of acrylamidopropyltrimethylammonium chloride and acrylic acid in a molar ratio from 60:40 to 95:5, and preferably from 75:25 to 90:10 in relation to each other;

cellulose 2-[2-hydroxy-3-(trimethylammonio)propoxy] ethyl ether chloride, which is available, for example, under the INCI name Polyquaternium-10, terpolymers of acrylic acid, diallyldimethylammonium chloride and acrylamide, such as are available, for example, under the INCI name Polyquaternium-39, homopolymers of N,N,N-trimethyl-2-[(methyl-1-oxo-2-propenyl)oxy]ethanaminium chloride, such as are available, for example, under the INCI name Polyquaternium-37, copolymers of diallyldimethylammonium chloride and acrylic acid, such as are available, for example, under the INCI name Polyquaternium-22, hydroxyethyl cellulose/diallyldimethylammonium chloride copolymers, such as are available, for example, under the INCI name Polyquaternium-4, copolymers of acrylamide and beta-methacryloyloxyethyl trimethyl ammonium methosulfate, such as are available, for example, under the INCI name Polyquaternium-5, homopolymers of N,N-dimethyl-N-2-propenyl-2-propene-1-aminium chloride, such as are available, for example, under the INCI name Polyquaternium-6, copolymers of diallyldimethylammonium chloride and acrylamide, such as are available, for example, under the INCI name Polyquaternium-7, copolymers of vinylpyrrolidone and dimethylaminoethyl methacrylate diethyl sulfate, such as are available, for example, under the INCI name Polyquaternium-11, and mixtures of the aforementioned polymers.

Permanently cationic polymers that are exceptionally preferred according to the invention are selected from cellulose 2-[2-hydroxy-3-(trimethylammonio)propoxy]ethyl ether chloride, amphoteric copolymers having a cationic net charge that are composed of acrylamidopropyltrimethylammonium chloride and acrylic acid in a molar ratio from 60:40 to 95:5, and preferably from 75:25 to 90:10 in relation to each other, and terpolymers of acrylic acid, diallyldimethylammonium chloride and acrylamide, and mixtures of two and three of these polymers.

Particularly preferred polymer B mixtures comprise cellulose 2-[2-hydroxy-3-(trimethylammonio)propoxy]ethyl ether chloride and at least one amphoteric copolymer having a cationic net charge that is composed of acrylamidopropyltrimethylammonium chloride and acrylic acid in a molar ratio from 60:40 to 95:5, and preferably from 75:25 to 90:10 in relation to each other.

Further particularly preferred polymer B mixtures comprise cellulose 2-[2-hydroxy-3-(trimethylammonio)propoxy]ethyl ether chloride, at least one amphoteric copolymer having a cationic net charge that is composed of acrylamidopropyltrimethylammonium chloride and acrylic acid in a molar ratio from 60:40 to 95:5, and preferably from 75:25 to 90:10 in relation to each other, and at least one terpolymer of acrylic acid, diallyldimethylammonium chloride and acrylamide.

Permanently cationic polymers B that are likewise exceptionally preferred according to the invention are selected from Polyquaternium-10, amphoteric copolymers having a cationic net charge that are composed of acrylamidopropyltrimethylammonium chloride and acrylic acid in a molar ratio from 60:40 to 95:5, and preferably from 75:25 to 90:10 in relation to each other, and Polyquaternium-39, and mixtures of two and three of these polymers.

Further particularly preferred polymer B mixtures comprise Polyquaternium-10 and at least one amphoteric copolymer having a cationic net charge that is composed of acrylamidopropyltrimethylammonium chloride and acrylic acid in a molar ratio from 60:40 to 95:5, and preferably from 75:25 to 90:10 in relation to each other.

Further particularly preferred polymer B mixtures comprise Polyquaternium-10 and at least one amphoteric copolymer having a cationic net charge that is composed of acrylamidopropyltrimethylammonium chloride and acrylic acid in a molar ratio from 60:40 to 95:5, and preferably from 75:25 to 90:10 in relation to each other, and Polyquaternium-39.

Preferred coloring or blonding agents according to the invention comprise the at least one permanently cationic polymer B in a total amount of 0.05 to 1.5 wt. %, preferably 0.1 to 1.0 wt. %, and particularly preferably 0.2 to 0.8 wt. %, in each case based on the weight of the coloring or blonding agent according to the invention.

Further coloring or blonding agents that are preferred according to the invention comprise at least one permanently cationic polymer B, selected from cationic polymers composed of monomers with quaternary ammonium groups of the general formula (IIa)

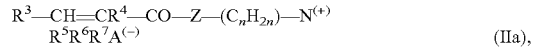

(IIa), in which $R^3$ and $R^4$, independently of one another, denote hydrogen or a methyl group, $R^5$, $R^6$ and $R^7$, independently of one another, denote an alkyl group having 1 to 4 carbon atoms, Z denotes an NH group or an oxygen atom, n denotes an integer from 2 to 4, and $A^{(-)}$ represents the anion of an inorganic or organic acid, preferably selected from cationic polymers composed of acrylamidopropyltrimethylammonium chloride, particularly preferably selected from amphoteric polymers having a cationic net charged, which by way of polymerization are composed of c) cationic monomers with quaternary ammonium groups of the general formula (IIa),

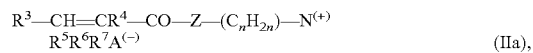

(IIa), in which $R^3$ and $R^4$, independently of one another, denote hydrogen or a methyl group, $R^5$, $R^6$ and $R^7$, independently of one another, denote an alkyl group having 1 to 4 carbon atoms, Z denotes an NH group or an oxygen atom, n denotes an integer from 2 to 4, and $A^{(-)}$ represents the anion of an inorganic or organic acid, and d) at least one unsaturated carboxylic acid, selected from acrylic acid, methacrylic acid, and crotonic acid, and mixtures of these acids, wherein the at least one unsaturated carboxylic acid may be present in the form of the salts thereof, wherein the collectivity of all cationic monomers is present in the polymer in a molar excess in relation to the collectivity of all anionic monomers;

exceptionally preferably selected from amphoteric polymers having a cationic net charge, which comprise the at least one monomer type of the general formula (IIa) and the at least one monomer type of the unsaturated carboxylic acid, selected from acrylic acid, methacrylic acid and crotonic acid, and mixtures thereof, in a molar ratio from 60:40 to 95:5, and preferably from 75:25 to 90:10 in relation to each other, exceptionally preferably selected from amphoteric copolymers having a cationic net charge, which are composed of acrylamidopropyltrimethylammonium chloride and acrylic acid in a molar ratio from 60:40 to 95:5, and preferably from 75:25 to 90:10 in relation to each other;

cellulose 2-[2-hydroxy-3-(trimethylammonio)propoxy] ethyl ether chloride, which is available, for example, under the INCI name Polyquaternium-10, terpolymers of acrylic acid, diallyldimethylammonium chloride and acrylamide, such as are available, for example, under the INCI name Polyquaternium-39, homopolymers of N,N,N-trimethyl-2-[(methyl-1-oxo-2-propenyl)oxy]ethanaminium chloride, such as are available, for example, under the INCI name Polyquaternium-37, copolymers of diallyldimethylammonium chloride and acrylic acid, such as are available, for example, under the INCI name Polyquaternium-22, hydroxyethyl cellulose/diallyldimethylammonium chloride copolymers, such as are available, for example, under the INCI name Polyquaternium-4, copolymers of acrylamide and beta-methacrylyloxyethyl trimethyl ammonium methosulfate, such as are available, for example, under the INCI name Polyquaternium-5, homopolymers of N,N-dimethyl-N-2-propenyl-2-propene-1-aminium chloride, such as are available, for example, under the INCI name Polyquaternium-6, copolymers of diallyldimethylammonium chloride and acrylamide, such as are available, for example, under the INCI name Polyquaternium-7, and copolymers of vinylpyrrolidone and dimethylaminoethyl methacrylate diethyl sulfate, such as are available, for example, under the INCI name Polyquaternium-11, in a total amount of 0.05 to 1.5 wt. %, preferably 0.1 to 1.0 wt. %, and particularly preferably 0.2 to 0.8 wt. %, in each case based on the weight of the coloring or blonding agent according to the invention.

Further coloring or blonding agents that are preferred according to the invention comprise cellulose 2-[2-hydroxy-3-(trimethylammonio)propoxy]ethyl ether chloride and at least one amphoteric copolymer having a cationic net charge that is composed of acrylamidopropyltrimethylammonium chloride and acrylic acid in a molar ratio from 60:40 to 95:5, and preferably from 75:25 to 90:10 in relation to each other, in a total amount of 0.05 to 1.5 wt. %, preferably 0.1 to 1.0 wt. %, and particularly preferably 0.2 to 0.8 wt. %, in each case based on the weight of the coloring or blonding agent according to the invention.

Further coloring or blonding agents that are preferred according to the invention comprise cellulose 2-[2-hydroxy-3-(trimethylammonio)propoxy]ethyl ether chloride, at least one amphoteric copolymer having a cationic net charge that is composed of acrylamidopropyltrimethylammonium chloride and acrylic acid in a molar ratio from 60:40 to 95:5, and preferably from 75:25 to 90:10 in relation to each other, and at least one terpolymer of acrylic acid, diallyldimethylammonium chloride, and acrylamide, in a total amount of 0.05 to 1.5 wt. %, preferably 0.1 to 1.0 wt. %, and particularly preferably 0.2 to 0.8 wt. %, in each case based on the weight of the coloring or blonding agent according to the invention.

Further particularly preferred coloring or blonding agents comprise Polyquaternium-10 and at least one amphoteric copolymer having a cationic net charge that is composed of acrylamidopropyltrimethylammonium chloride and acrylic acid in a molar ratio from 60:40 to 95:5, and preferably from 75:25 to 90:10 in relation to each other, in a total amount of 0.05 to 1.5 wt. %, preferably 0.1 to 1.0 wt. %, and particularly preferably 0.2 to 0.8 wt. %, in each case based on the weight of the coloring or blonding agent according to the invention.

Further particularly preferred coloring or blonding agents comprise Polyquaternium-10 and at least one amphoteric copolymer having a cationic net charge that is composed of acrylamidopropyltrimethylammonium chloride and acrylic acid in a molar ratio from 60:40 to 95:5, and preferably from 75:25 to 90:10 in relation to each other, and Polyquaternium-39 in a total amount of 0.05 to 1.5 wt. %, preferably 0.1 to 1.0 wt. %, and particularly preferably 0.2 to 0.8 wt. %, in each case based on the weight of the coloring or blonding agent according to the invention.

Amino Acid

Amino acids are another important component of the active repair substance combination according to the invention in the coloring or blonding agents according to the invention. Coloring or blonding agents according to the invention comprise at least one amino acid. Amino acids that are preferred according to the invention are selected from serine, arginine, alanine, asparagine, aspartic acid, cysteine, glutamine, glutamic acid, glycine, histidine, isoleucine, leucine, lysine, methionine, phenylalanine, proline, threonine, tryptophan, tyrosine and valine, and mixtures of these amino acids.

Surprisingly, it was found that a content of at least one amino acid, which is preferably selected from serine, arginine, alanine, asparagine, aspartic acid, cysteine, glutamine, glutamic acid, glycine, histidine, isoleucine, leucine, lysine, methionine, phenylalanine, proline, threonine, tryptophan, tyrosine and valine, and mixtures of these amino acids, brings with it a particularly low damaging effect on the hair of the coloring or blonding agents according to the invention.

A particularly high protective action was found in particular for serine, arginine, histidine and lysine, and for mixtures thereof. Exceptionally preferred coloring or blonding agents according to the invention include serine and at least one of the basic amino acids arginine, histidine or lysine, wherein particularly preferably serine and at least one of the basic amino acids arginine, histidine or lysine are present in a molar ratio of serine to basic amino acids overall in the range from 1:1 to 50:1, and preferably 5:1 to 30:1.

Coloring or blonding agents that are preferred according to the invention are thus characterized in that the at least one amino acid is selected from serine, arginine, histidine and lysine, and mixtures thereof, wherein preferably serine and at least one of the basic amino acids arginine, histidine or lysine are present, and wherein particularly preferably serine and at least one of the basic amino acids arginine, histidine or lysine are present in a molar ratio of serine to basic amino acids overall in the range from 1:1 to 50:1, and preferably 5:1 to 30:1.

Further coloring or blonding agents that are preferred according to the invention are characterized in that the at least one amino acid is present in a total amount of 0.5 to 5 wt. %, preferably 0.7 to 3 wt. %, and particularly preferably 0.9 to 2 wt. %, in each case based on the weight of the coloring or blonding agent.

Further coloring or blonding agents that are preferred according to the invention are characterized in that a mixture of serine and at least one of the basic amino acids arginine, histidine or lysine is present in a total amount of 0.5 to 5 wt. %, preferably 0.7 to 3 wt. %, and particularly preferably 0.9 to 2 wt. %, each based on the weight of the coloring or blonding agent, wherein particularly preferably serine and at least one of the basic amino acids arginine, histidine or lysine are present in a molar ratio of serine to basic amino acids overall in the range from 1:1 to 50:1, and preferably 5:1 to 30:1.

Surprisingly, it was furthermore found that the hair-protecting action of the coloring or blonding agents according to the invention and of the preferred coloring or blonding agents according to the invention can be further increased if at least one compound of the general formula (III) is present.

Further coloring or blonding agents that are preferred according to the invention thus comprise i. at least one compound of the general formula (III),

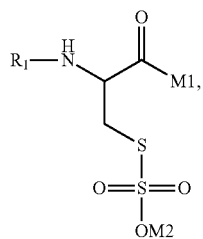

(III)

wherein
R1 denotes a hydrogen atom or a structural element of formula (IV)

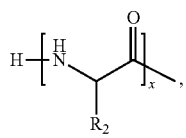

(IV)

wherein
x denotes an integer from 1 to 100,
the group R2 in each of the structural elements of formula (IV) can each be selected independently of the preceding structural element of formula (IV),
R2 denotes a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group,
M1 denotes the group —OM2 or a structural element of formula (V),

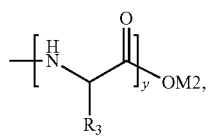

(V)

wherein
y denotes an integer from 1 to 100,
the group R3 in each of the structural elements of formula (V) can each be selected independently of the preceding structural element of formula (V),
R3 denotes a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group, M2 denotes a hydrogen atom, an equivalent of a monovalent or polyvalent cation, or an ammonium ion $(NH_4)^+$.

The ingredient (a) of formula (III) essential to the invention is the Bunte salt of an amino acid, an oligopeptide or a peptide, which represents a compound of formula (III),

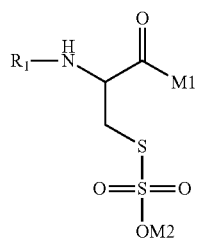

(III)

wherein
R1 denotes a hydrogen atom or a structural element of formula (IV)

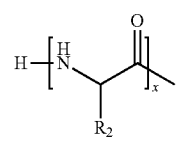

(IV)

wherein
x denotes an integer from 1 to 100,
the group R2 in each of the structural elements of formula (IV) can each be selected independently of the preceding structural element of formula (IV),
R2 denotes a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group,
M1 denotes the group —OM2 or a structural element of formula (V),

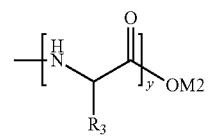

(V)

wherein
y denotes an integer from 1 to 100,
the group R3 in each of the structural elements of formula (V) can each be selected independently of the preceding structural element of formula (V),
R3 denotes a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group, M2 denotes a hydrogen atom, an equivalent of a monovalent or polyvalent cation, or an ammonium ion $(NH_4)^+$.

The group R1 can either denote a hydrogen atom or a structural element of formula (IV)

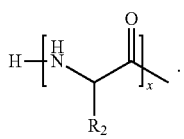

(IV)

The structural element of formula (IV) is furthermore characterized by the repetition index x, wherein x denotes an integer from 1 to 100. The repetition index x indicates the number of structural elements of formula (IV) present in the compound of formula (III).

The letter x preferably denotes an integer from 1 to 50, more preferably x denotes an integer from 1 to 20, and especially particularly preferably x denotes an integer from 1 to 10.

If x denotes the number 10, for example, the compound of formula (III) comprises 10 structural elements of formula (IV).

What is essential here is that the group R2 in each of the structural elements of formula (IV) can each be selected independently of the preceding structural element of formula (IV). If the compounds of formula (III) comprise 10 structural units of formula (IV), for example, these 10 structural units may be identical, or else they may be different from each other.

The group R2 denotes a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group.

The structural element of formula (IV) is thus an amino acid that is peptidically linked via the amino function thereof and/or the acid function thereof within the compound of formula (III). If the amino acid is cysteine, this may also be present in the form of a Bunte salt.

If the group R2 denotes a hydrogen atom, the structural element of formula (IV) is based on the amino acid glycine.

If the group R2 denotes a methyl group, the structural element of formula (IV) is based on the amino acid alanine.

If the group R2 denotes an isopropyl group (which is to say a $(H_3C)_2CH-$ group), the structural element of formula (IV) is based on the amino acid valine.

If the group R2 denotes a 2-methylpropyl group (which is to say a $(H_3C)_2CH-CH_2-$ group), the structural element of formula (IV) is based on the amino acid leucine.

If the group R2 denotes a 1-methylpropyl group (which is to say a $(H_3C)_2CH-CH_2-$ group), the structural element of formula (IV) is based on the amino acid isoleucine.

If the group R2 denotes a benzyl group (which is to say a $C_6H_5-CH_2-$ group), the structural element of formula (IV) is based on the amino acid phenylalanine.

If the group R2 denotes a 4-hydroxybenzyl group (which is to say a $4-OH-C_6H_5-CH_2-$ group), the structural element of formula (IV) is based on the amino acid tyrosine.

If the group R2 denotes a hydroxymethyl group (which is to say a (H3C)2CH— group), the structural element of formula (IV) is based on the amino acid serine.

If the group R2 denotes a 1-hydroxyethyl group (which is to say a (H3C—CH(OH)— group), the structural element of formula (IV) is based on the amino acid threonine.

If the group R2 denotes a 4-aminobutyl group (which is to say a H2N—CH2-CH2-CH2-CH2- group), the structural element of formula (IV) is based on the amino acid lysine.

If the group R2 denotes a 3-carbamimidamidopropyl group (which is to say a H2N—C(NH)—NH—CH2—CH2—CH2— group), the structural element of formula (IV) is based on the amino acid arginine.

If the group R2 denotes a 2-carboxyethyl group (which is to say a HOOC—CH2-CH2- group), the structural element of formula (IV) is based on the amino acid glutamic acid.

If the group R2 denotes a carboxymethyl group (which is to say a HOOC—CH2- group), the structural element of formula (IV) is based on the amino acid aspartic acid.

If the group R2 denotes a 2-carbamoylethyl group (which is to say a H2N—C(O)—CH2-CH2- group), the structural element of formula (IV) is based on the amino acid glutamine.

If the group R2 denotes a 2-carbamoylethyl group (which is to say a H2N—C(O)—CH2- group), the structural element of formula (IV) is based on the amino acid asparagine.

If the group R2 denotes a sulfanylmethyl group (which is to say a HS—CH2- group), the structural element of formula (IV) is based on the amino acid cysteine.

If the group R2 denotes a 2-(methylsulfanyl)ethyl group (which is to say a H3C—S—CH2-CH2- group), the structural element of formula (IV) is based on the amino acid methionine.

If the group R2 denotes a 1H-imidazole-4-ylmethyl group, the structural element of formula (IV) is based on the amino acid histidine.

If the group R2 denotes a 1H-indole-3-ylmethyl group, the structural element of formula (IV) is based on the amino acid tryptophan.

Finally, the group R2 may also denote a (sulfosulfanyl)methyl group, which involves a Bunte salt structure of formula $HO-S(O_2)-S-CH_2-$.

Depending on the pH value of the coloring or blonding agent, the Bunte salt structure of formula $HO-S(O_2)-S-CH_2-$ may also be present in the deprotonated form thereof.

Within the compound of formula (III), M1 denotes the group —OM2 or a structural element of formula (V)

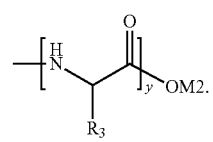

(V)

Similarly to the structural element of formula (IV), the structural element of formula (V) is characterized by the repetition index y, wherein y denotes an integer from 1 to 100. The repetition index y indicates the number of structural elements of formula (V) present in the compound of formula (III).

The letter y preferably denotes an integer from 1 to 50, more preferably y denotes an integer from 1 to 20, and especially particularly preferably y denotes an integer from 1 to 10.

If y denotes the number 10, for example, the compound of formula (III) comprises 10 structural elements of formula (V).

What is essential here is that the group R3 in each of the structural elements of formula (V) can each be selected independently of the preceding structural element of formula (V). If the compounds of formula (III) comprise 10 structural units of formula (V), for example, these 10 structural units may be identical, or else they may be different from each other.

The group R3 denotes a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group.

The structural element of formula (V) is thus also an amino acid that is peptidically linked via the amino function thereof and/or the acid function thereof within the compound of formula (III). If the amino acid is cysteine, this may also be present in the form of a Bunte salt.

If the group R3 denotes a hydrogen atom, the structural element of formula (IV) is based on the amino acid glycine.

If the group R3 denotes a methyl group, the structural element of formula (IV) is based on the amino acid alanine.

If the group R3 denotes an isopropyl group (which is to say a $(H_3C)_2CH—$ group), the structural element of formula (IV) is based on the amino acid valine.

If the group R3 denotes a 2-methylpropyl group (which is to say a $(H_3C)_2CH—CH_2—$ group), the structural element of formula (IV) is based on the amino acid leucine.

If the group R3 denotes a 1-methylpropyl group (which is to say a (H3C)2CH—CH2- group), the structural element of formula (IV) is based on the amino acid isoleucine.

If the group R3 denotes a benzyl group (which is to say a $C_6H_5—CH_2—$ group), the structural element of formula (IV) is based on the amino acid phenylalanine.

If the group R3 denotes a 4-hydroxybenzyl group (which is to say a $4OH—C_6H_5—CH_2—$ group), the structural element of formula (IV) is based on the amino acid tyrosine.

If the group R3 denotes a hydroxymethyl group (which is to say a (H3C)2CH— group), the structural element of formula (IV) is based on the amino acid serine.

If the group R3 denotes a 1-hydroxyethyl group (which is to say a (H3C—CH(OH)— group), the structural element of formula (IV) is based on the amino acid threonine.

If the group R3 denotes a 4-aminobutyl group (which is to say a H2N—CH2-CH2-CH2-CH2- group), the structural element of formula (IV) is based on the amino acid lysine.

If the group R3 denotes a 3-carbamimidamidopropyl group (which is to say a $H_2N—C(NH)—NH—CH_2—CH_2—CH_2—$ group), the structural element of formula (IV) is based on the amino acid arginine.

If the group R3 denotes a 2-carboxyethyl group (which is to say a HOOC—CH2-CH2- group), the structural element of formula (IV) is based on the amino acid glutamic acid.

If the group R3 denotes a carboxymethyl group (which is to say a HOOC—CH2- group), the structural element of formula (IV) is based on the amino acid aspartic acid.

If the group R3 denotes a 2-carbamoylethyl group (which is to say a H2N—C(O)—CH2-CH2- group), the structural element of formula (IV) is based on the amino acid glutamine.

If the group R3 denotes a 2-carbamoylethyl group (which is to say a H2N—C(O)—CH2- group), the structural element of formula (IV) is based on the amino acid asparagine.

If the group R3 denotes a sulfanylmethyl group (which is to say a HS—CH2- group), the structural element of formula (IV) is based on the amino acid cysteine.

If the group R3 denotes a 2-(methylsulfanyl)ethyl group (which is to say a H3C—S—CH2-CH2- group), the structural element of formula (IV) is based on the amino acid methionine.

If the group R3 denotes a 1H-imidazole-4-ylmethyl group, the structural element of formula (IV) is based on the amino acid histidine.

If the group R3 denotes a 1H-indole-3-ylmethyl group, the structural element of formula (IV) is based on the amino acid tryptophan.

Finally, the group R3 may also denote a (sulfosulfanyl)methyl group, which involves a Bunte salt structure of formula $HO—S(O_2)—S—CH_2—$.

Depending on the pH value of the coloring or blonding agent, the Bunte salt structure of formula $HO—S(O_2)—S—CH_2—$ may also be present in the deprotonated form thereof here.

The group M2 denotes a hydrogen atom, an equivalent of a monovalent or polyvalent cation, or an ammonium ion $(NH_4)^+$.

In particular, the cations of sodium and potassium ($Na^+$ and $K^+$) or else of magnesium or calcium (½ $Mg^{2+}$ or ½ $Ca^{2+}$) may be mentioned as preferred equivalents of a monovalent or polyvalent cation.

If M2 denotes a hydrogen atom, the —OM2 group involves the —OH group. If M2 denotes a sodium cation, the —OM2 group involves the —ONa group. If M2 denotes a potassium cation, the —OM2 group involves the —OK group. If M2 denotes an ammonium ion, the —OM2 group involves the —O(NH4) group.

The —OM2 group always adjoins a carbonyl group. In sum, if M2 denotes H, K, Na or ammonium, in the compound of formula (III) is thus either present in the form of an acid in the protonated form thereof, or the sodium, potassium or ammonium salt of this acid.

The compounds of formula (III) according to the invention are either the Bunte salt of the amino acid cysteine, the Bunte salts of oligopeptides, or else the Bunte salts of peptides.

When R1 denotes a hydrogen atom and the group M1 denotes an —OM2 group, the compound of formula (III) is the Bunte salt of the amino acid cysteine. In this case, the compound of formula (III) is the compound of formula (IIIa),

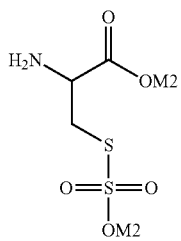
(IIIa)

wherein M2 is again defined as described above.

If the compound of formula (IIIa) is present in the form of the free acid thereof, then this involves 2-amino-3-(sulfosulfanyl)propanoic acid. This substance is commercially available.

It was found that the use of the compound of formula (IIIa) in coloring or blonding agents results in a particularly effective reduction in damage to the hair already at particularly low amounts, and that this reduction is still present even after washing the hair several times. The use of compounds of formula (IIIa) in coloring or blonding agents is therefore especially particularly preferred.

In an especially particularly preferred embodiment, a coloring or blonding agent according to the invention is characterized by comprising at least one compound of formula (III), wherein
R1 denotes a hydrogen atom, and
M1 denotes an —OM2 group.

When a compound of formula (IIIa) is used, this preferably involves the use of this specific compound. However, if the Bunte salts of oligopeptides are used as compounds of formula (III), the coloring or blonding agent according to the invention can also comprise several compounds of formula (III) in the form of a mixture of different oligopeptides. These oligopeptides are defined by the average molecular weight thereof. The average molecular weight $M_w$ of the at least one oligopeptide of formula (III) can be determined, for example, by way of gel permeation chromatography (GPC) using polystyrene as the internal standard in accordance with DIN 55672-3, Version 8/2007.

Depending on the number of structural elements of formula (III) and/or (IV) present in the compound of formula (III), and depending on the type of these amino acids, the molecular weight of the compound of formula (III) used according to the invention may vary. It is particularly preferred according to the invention if the compound of formula (III) is an oligopeptide that has a molecular weight $M_w$ of 200 to 2,000 Da, especially of 250 to 1,500 Da, preferably of 300 to 1.200 Da, and in particular of 400 to 800 Da.

The term oligopeptide within the scope of the present invention shall be understood to mean condensation products of amino acids that have the above-described molecular weights.

In an especially particularly preferred embodiment, a coloring or blonding agent according to the invention is characterized by comprising at least one compound of formula (III) that has a molecular weight $M_w$ of 200 to 2,000 Da (Dalton), especially of 250 to 1,500 Da, preferably of 300 to 1,200 Da, and in particular of 400 to 800 Da.

If a mixture of oligomers is used in the coloring or blonding agent according to the invention, these mixtures may also be defined by way of the average molecular weights thereof.

In this case, a preferred coloring or blonding agent according to the invention is characterized by comprising at least one mixture of compounds of formula (III) that has an average molecular weight $M_w$ of 200 to 2,000 Da, especially of 250 to 1,500 Da, preferably of 300 to 1,200 Da, and in particular of 400 to 800 Da.

Furthermore, it was found that the protective or repair effect of the compounds of formula (III) is also dependent on the repetition indices x and y. As described above, it is especially particularly preferred when x denotes an integer from 1 to 10, and y denotes an integer from 1 to 10.

In a further especially particularly preferred embodiment, a coloring or blonding agent according to the invention is characterized by comprising at least one compound of formula (III), wherein
R1 denotes a structural element of formula (IV), and
M1 denotes a structural element of formula (V), and
x denotes an integer from 1 to 10; and
y denotes an integer from 1 to 10.

In addition to the molecular weight of the compound of formula (III), the content of the Bunte salts units present in the compound of formula (III) also decisively influences the effectiveness of the protective action or "repair action" of the compounds.

Compounds having at least one Bunte salt unit, such as is present in the compound of formula (IIIa), for example, are very effective, in particular when they are used as a monomeric compound. Oligopeptides having at least one Bunte salt unit are particularly effective when they have a low molecular weight of up to 1200 dalton, and in particular 800 dalton.

When oligopeptides are used, however, it is especially particularly advantageous when the compound of formula (III) includes at least two, and preferably at least three, Bunte salt units.

In a further especially particularly preferred embodiment, a coloring or blonding agent according to the invention is characterized by comprising at least one compound of formula (III), wherein
R1 denotes a structural element of formula (IV), and
the group R2 denotes a (sulfosulfanyl)methyl group (which is to say a HO—S(O$_2$)—S—CH$_2$— group) in at least one structural element of formula (IV).

In a further especially particularly preferred embodiment, a coloring or blonding agent according to the invention is characterized by comprising at least one compound of formula (III), wherein
R1 denotes a structural element of formula (IV), and
x denotes an integer of at least 3; and
the group R2 denotes a 2-carboxyethyl group (which is to say a HOOC—CH2-CH2- group) in at least 3 structural elements of formula (IV).

In a further especially particularly preferred embodiment, a coloring or blonding agent according to the invention is characterized by comprising at least one compound of formula (III), wherein
M1 denotes a structural element of formula (V), and
y denotes an integer of at least 3, and
the group R3 denotes a (Glu) group in at least 3 structural elements of formula (IV).

The at least one compound of formula (III) is present in a total amount of 0.001 to 10 wt. %, based on the total weight of the coloring or blonding agent according to the invention, or the preferred coloring or blonding agent according to the invention. Surprisingly, however, it was found that the compound(s) of formula (III) can bring about an excellent reduction in damage to the hair already in low concentrations. This is in particular advantageous when the at least one compound of formula (III) is to be added to the coloring or blonding agent according to the invention as an additive (for example in the form of a nourishing lotion or repair lotion) prior to being applied to the hair. For this reason, it is particularly advantageous if the coloring or blonding agent according to the invention comprises one or more compounds of the above-described formula (III) in a total amount of 0.001 to 2.5 wt. %, more preferably of 0.01 to 1.0 wt. %, and particularly preferably of 0.02 to 0.1 wt. %, in each case based on the weight of the coloring or blonding agent according to the invention.

In a further especially particularly preferred embodiment, a coloring or blonding agent according to the invention is characterized by comprising one or more compounds of the above-described formula (III) in a total amount of 0.001 to 2.5 wt. %, more preferably of 0.01 to 1.0 wt. %, and particularly preferably of 0.02 to 0.1 wt. %, in each case based on the weight of the coloring or blonding agent according to the invention.

Alkalizing Agent

The coloring or blonding agents according to the invention furthermore comprise at least one alkalizing agent, selected from ammonium hydroxide, monoethanolamine and sodium silicates, and mixtures thereof.

So as to achieve the desired permanent coloration or lightening of the keratin fibers, the coloring or blonding agent according to the invention can have a pH value in the range of 6.5 to 11.0, preferably 8 to 10.5, and particularly preferably 8.5 to 10, each measured at 20° C. At these pH values, the outer keratin fiber layer opens optimally to receive the oxidation dye precursors, and the desired action of the peroxide compound develops optimally.

Ammonia is preferably used in the form of the aqueous solution thereof. Corresponding aqueous ammonia solutions may be 10 to 35 percent solutions (calculated in wt. %, 100 g aqueous ammonia solution accordingly comprises 10 to 35 g ammonia). Ammonia is preferably used in the form of a 20 to 30 wt. % solution, and particularly preferably in the form of a 25 wt. % solution.

For the coloring agents according to the invention to meet the expected requirements profile in terms of the color intensity and the color fastness properties thereof, the use of ammonia is indispensable.

In a particularly preferred embodiment, the coloring or blonding agent according to the invention is characterized by comprising ammonium hydroxide in an amount of 0.20 to 2.5 wt. %, preferably of 0.5 to 2.0 wt. %, more preferably of 1.0 to 1.5 wt. %, and particularly preferably of 0.31 to 0.8 wt. %, based on the total weight of the coloring or blonding agent according to the invention.

In addition to, or instead of, ammonium hydroxide, preferred coloring or blonding agents according to the invention comprise monoethanolamine.

So as to achieve maximum odor masking and optimize the fastness properties, monoethanolamine is present in a total amount of 0.2 to 6.5 wt. %, preferably of 0.5 to 4.0 wt. %, more preferably of 0.7 to 2.5 wt. %, and particularly preferably of 0.8 to 1.6 wt. %, based on the total weight of the coloring or blonding agent according to the invention.

Sodium silicates within the meaning of the present invention are chemical compounds that are composed of sodium oxide and silicon dioxide and can be present in various molar ratios (monosilicate, metasilicate and polysilicate). One example of a sodium silicate is the sodium salt of orthosilicic acid having the empirical formula $Na_4SiO_4$, which is also referred to as sodium orthosilicate.

Further examples of suitable sodium silicates are the disodium metasilicate or sodium metasilicate having the empirical formula $Na_2SiO_3$, the disodium disilicate having the empirical formula $Na_2Si_2O_5$, or the disodium trisilicate having the empirical formula $Na_2Si_3O_7$.

Silicates in amorphous form can be produced by fusing silicon dioxide and alkali oxide in molar ratios between 1:1 and 4:1. The solids thus obtained are dissolved at approximately 150° C. and a vapor pressure of 5 bar so as to obtain a solution of the sodium silicates in water; these corresponding solutions are alkali sodium silicates.

Alkali sodium silicates is the term used for vitreous (amorphous) sodium silicates or the aqueous solutions thereof, solidified from a melt. These are also referred to as sodium water glasses. The definition of the sodium silicates within the present invention also covers sodium water glasses.

The molar composition of water glasses is usually 2 to 4 moles $SiO_2$ for 1 mole alkali oxide ($Na_2O$).

One example of a preferred sodium silicate is sodium water glass that is present in the form of the aqueous solution thereof, has a $Na_2O$ content of 7.5 to 8.8 wt. %, and an SiO2 content of 25.0 to 28.5 wt. %, and has the CAS number 1344-09-5 (Chemical Abstracts number).

Further coloring or blonding agents that are preferred according to the invention comprise at least one sodium silicate in a total amount of 0.1 to 9 wt. %, preferably 0.2 to 8 wt. %, and particularly preferably 1 to 7.5 wt. %, in each case based on the total weight of the coloring or blonding agent according to the invention.

Furthermore, other alkalizing agents, such as potassium hydroxide (KOH) and sodium hydroxide (NaOH), may be present, typically in a total amount of 0.05 to 1.5 wt. %, and preferably 0.1 to 0.6 wt. %, in each case based on the total weight of the coloring or blonding agent according to the invention.

To the extent that the agents according to the invention are agents for oxidatively coloring keratin fibers, and in particular human hair, these comprise at least one oxidation dye precursor for forming the dyes.

Oxidation dye precursors cover oxidation dye precursors of the developer type and of the coupler type. Particularly suitable oxidation dye precursors of the developer type are selected from at least one compound from the group consisting of p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazole-1-yl)propyl]amine, N,N'-bis-(2-hydroxyethyl)-N,N'-bis-(4-aminophenyl)-1,3-diamino-propane-2-ol, bis(2-hydroxy-5-aminophenyl)methane, 1,3-bis-(2,5-diaminophenoxy)-propane-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H, 5H-pyrazolo[1,2-a]pyrazole-1-on, and the physiologically compatible salts thereof.

Particularly suitable oxidation dye precursors of the coupler type are selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)- amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholine-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazole-5-on, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline, or mixtures of these compounds or the physiologically compatible salts thereof.

In a preferred embodiment, the coloring agents according to the invention comprise one or more oxidation dye precursors in a total amount of 0.01 to 4.0 wt. %, preferably of 0.1 to 3.5 wt. %, more preferably of 0.6 to 3.1 wt. %, and especially particularly preferably of 1.2 to 2.2 wt. %, based on the total weight of the coloring or blonding agent according to the invention.

In a further preferred embodiment, the agents according to the invention additionally comprise at least one further direct dye. Direct dyes can be broken down into anionic, cationic and non-ionic direct dyes. The direct dyes are preferably selected from the nitrophenylenediamines, the nitroaminophenols, the azo dyes, the anthraquinones, the triarylmethane dyes or the indophenols, and the physiologically compatible salts thereof. The respective direct dyes are preferably present in a total amount of 0.001 to 2 wt. %, based on the total weight of the coloring or blonding agent according to the invention. Direct dyes are used in oxidative coloring agents to nuance the hue that is achieved, and in oxidative blonding agents to compensate for undesirable red hues that may be created during the depletion of melanin naturally present in hair.

Preferred anionic direct dyes are the compounds known under the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic direct dyes are cationic triphenylmethane dyes, such as Basic Blue 7, Basic Blue 26, Basic Violet 2 and Basic Violet 14, aromatic systems substituted with a quaternary nitrogen group, such as Basic Yellow 57, Basic Red 76, Basic Blue 99, Basic Brown 16 and Basic Brown 17, cationic anthraquinone dyes such as HC Blue 16 (Bluequat B), and direct dyes that include a heterocycle having at least one quaternary nitrogen atom, in particular Basic Yellow 87, Basic Orange 31 and Basic Red 51. The cationic direct dyes that are sold under the trademark Arianor are cationic direct dyes that are likewise preferred according to the invention.

In particular non-ionic nitro and quinone dyes and neutral azo dyes are suited as non-ionic direct dyes. Preferred non-ionic direct dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 11, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

Water

The coloring or blonding agents according to the invention comprise water in an amount of 20 to 85 wt. %, and preferably 30 to 80 wt. %, in each case based on the total weight of the coloring or blonding agent according to the invention.

Peroxide Compounds

The formation of the dyes in oxidative coloring agents, or the depletion of melanin, the pigment that gives hair its color, for blonding requires the influence of a peroxide compound as an oxidizing agent. Usually, hydrogen peroxide is used for this purpose. Hydrogen peroxide can only be used in the form of an aqueous solution.

Coloring or blonding agents that are preferred according to the invention are characterized by comprising 0.5 to 13 wt. %, more preferably 1 to 7 wt. %, particularly preferably 2 to 6 wt. %, and especially particularly preferably 3 to 4.5 wt. % hydrogen peroxide (calculated as 100% $H_2O_2$), in each case based on the total weight of the coloring or blonding agent according to the invention.

Blonding agents, or coloring agents that have a particularly strong lightening effect, can additionally comprise strongly oxidizing peroxide compounds, such as potassium, sodium and/or ammonium persulfate.

It has proven advantageous for the oxidizing agent preparations according to the invention to additionally comprise at least one stabilizer or complexing agent so as to stabilize the hydrogen peroxide. Particularly preferred stabilizers are in particular EDTA and EDDS, and phosphonates, in particular 1-hydroxyethane-1,1-diphosphonate (HEDP) and/or ethylenediamine tetramethylene phosphonate (EDTMP) and/or diethylenetriamine pentamethylene phosphonate (DTPMP), or the sodium salts thereof.

A further subject matter of the present invention is a method for oxidatively coloring and/or lightening keratin fibers, and in particular human hair, in which a coloring or blonding agent, comprising a) at least one polymer, which includes at least ten constitutional units of formula (I),

where

X denotes nitrogen or oxygen, and $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, which are preferably selected from N and O, and/or optionally is substituted with at least one C1 to C6 alkyl group and/or with at least one functional group, and p=0 when X denotes oxygen, and p=1 when X denotes nitrogen, b) furthermore comprising at least one permanently cationic polymer, c) furthermore at least one amino acid, d) furthermore at least one alkalizing agent, selected from ammonium hydroxide, monoethanolamine and sodium silicates, and mixtures thereof, e) optionally at least one oxidation dye precursor and/or at least one direct dye, f) water, and g) at least one peroxide compound, or a preferred coloring or blonding agent according to any one of claims 2 to 10, is applied to the keratin fibers, and in particular to the human hair, and is rinsed off again after an exposure time of 1 to 60 minutes.

The method according to the invention for oxidatively coloring and/or lightening keratin fibers, and in particular human hair, may optionally be followed by further hair treatment steps, such as the application of a conditioner, a hair styling agent, such as a straightening agent or a perming agent, a further hair coloring agent, for example for coloring or blonding highlights, rinsing steps, and drying steps, for example for rubbing dry or pressing dry by way of a towel, blow drying, or drying by way of a hood dryer.

What was said above with respect to the coloring and blonding agents according to the invention and preferred coloring and blonding agents according to the invention applies, mutatis mutandis, to the method according to the invention for oxidatively coloring and/or lightening keratin fibers, and in particular human hair, and the preferred embodiments thereof.

It may be preferred according to the invention to initially store the hair-protecting combination according to the invention, composed of a select polymer, a permanently cationic polymer and at least one amino acid, separately from the preparation comprising the at least one alkalizing agent and optionally at least one oxidation dye precursor and/or at least one direct dye, and separately from the oxidizing agent preparation comprising at least one peroxide compound, and to prepare the coloring or blonding agent according to the invention, or the preferred coloring or blonding agent according to the invention, just prior to starting the method according to the invention, or the preferred method according to the invention, by mixing the three components.

A further subject matter of the present invention is thus a method for oxidatively coloring and/or lightening keratin fibers, and in particular human hair, comprising the following method steps:

I. providing a composition (A), comprising a) at least one polymer, which includes at least ten constitutional units of formula (I),

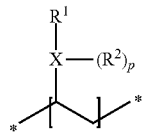

where

X denotes nitrogen or oxygen, and $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, which are preferably selected from N and O, and/or optionally is substituted with at least one C1 to C6 alkyl group and/or with at least one functional group, and p=0 when X denotes oxygen, and p=1 when X denotes nitrogen, b) furthermore comprising at least one permanently cationic polymer, c) furthermore at least one amino acid, d) water, II. providing a composition (B), comprising e) at least one alkalizing agent, selected from ammonium hydroxide, monoethanolamine and sodium silicates, and mixtures thereof, f) water, and g) optionally at least one oxidation dye precursor and/or at least one direct dye, III. providing a composition (C), comprising h) at least one peroxide compound, which preferably is hydrogen peroxide, IV. mixing compositions (A), (B) and (C) with each other, immediately thereafter V. applying the mixture of (A), (B) and (C) to the keratin fibers, and in particular to the human hair, and VI. rinsing after an exposure time of 1 to 60 minutes, VII. optionally further heat treatments, such as styling, conditioning and/or drying.

Mixing Ratios of Composition (A), Composition (B) and Composition (C)

It has proven useful according to the invention if the weight ratio of composition (A), which comprises the hair-protecting combination composed of at least one polymer, which includes at least ten constitutional units of formula (I), furthermore at least one permanently cationic polymer, at least one amino acid and water, to the oxidatively coloring and/or oxidatively lightening mixture of composition (B), comprising at least one alkalizing agent, and optionally oxidation dye precursors and/or direct dyes, and composition (C), comprising at least one peroxide compound, is in the range of [weight of A]/[weight of B+weight of C] of 1:5 to 1:10, preferably 1:4 to 1:9, and particularly preferably 1:7 to 1:9.

Coloring or lightening methods that are preferred according to the invention using the at least three aforementioned compositions (A), (B), and (C) are characterized in that the at least one polymer A including at least ten constitutional units of formula (I) is present in composition (A) in a total amount of 1.0 to 25 wt. %, preferably 3 to 15 wt. %, and particularly preferably 5 to 10.5 wt. %, in each case based on the weight of composition (A).

Coloring or lightening methods that are preferred according to the invention using the at least three aforementioned compositions (A), (B), and (C) are furthermore characterized in that the at least one permanently cationic polymer B is present in composition (A) in a total amount of 0.4 to 5.0 wt. %, preferably 0.5 to 2.0 wt. %, and particularly preferably 0.6 to 1.5 wt. %, in each case based on the weight of composition (A).

Coloring or lightening methods that are preferred according to the invention using the at least three aforementioned compositions (A), (B), and (C) are furthermore characterized in that the at least one amino acid is present in composition (A) in a total amount of 0.5 to 10 wt. %, preferably 1.0 to 7 wt. %, and particularly preferably 2.0 to 5.5 wt. %, in each case based on the weight of composition (A).

Further coloring or lightening methods that are preferred according to the invention using the at least three aforementioned compositions (A), (B), and (C) are characterized in that a mixture of serine and at least one of the basic amino acids arginine, histidine or lysine is present in composition (A) in a total amount of 0.5 to 10 wt. %, preferably 1.0 to 7 wt. %, and particularly preferably 2.0 to 5.5 wt. %, each based on the weight of composition (A), wherein particularly preferably serine and at least one of the basic amino acids arginine, histidine or lysine are present in a molar ratio of serine to basic amino acids overall in the range from 1:1 to 50:1, and preferably 5:1 to 30:1.

Further coloring or lightening methods that are preferred according to the invention using the at least three aforementioned compositions (A), (B), and (C) are characterized in that composition (A) comprises one or more compounds of above-mentioned formula (III) in a total amount of 0.01 to 5 wt. %, more preferably 0.05 to 1.0 wt. %, and particularly preferably 0.1 to 0.5 wt. %, in each case based on the weight of composition (A).

Further coloring or lightening methods that are preferred according to the invention using the at least three aforementioned compositions (A), (B), and (C) are characterized in that composition (A) comprises 50 to 92 wt. %, preferably 60 to 87 wt. %, and particularly preferably 70 to 83 wt. % water, in each case based on the weight of composition (A).

Further coloring or lightening methods that are preferred according to the invention using the at least three aforementioned compositions (A), (B) and (C) are characterized in that composition (A) has a pH value in the range of 3.5 to 7.1, preferably 4.5 to 6.5, and particularly preferably 5.0 to 6.0, each measured at 20° C.

Further coloring or lightening methods that are preferred according to the invention using the at least three aforementioned compositions (A), (B) and (C) are characterized in that composition (C) comprises 1.0 to 23.0 wt. %, more preferably 2.5 to 21.0 wt. %, particularly preferably 4.0 to 20.0 wt. %, and especially particularly preferably 5.0 to 18.0 wt. % hydrogen peroxide (calculated as 100% $H_2O_2$), in each case based on the total weight of composition (C).

Apart from the modified quantitative information cited above, what was said above with respect to the coloring and blonding agents according to the invention and the preferred coloring and blonding agents according to the invention applies, mutatis mutandis, to the method according to the invention for oxidatively coloring and/or lightening keratin fibers, and in particular human hair, using the at least three above-described compositions (A), (B) and (C), and the preferred embodiments thereof.

It may furthermore be preferred according to the invention to initially store the hair-protecting combination according to the invention, composed of a select polymer, a permanently cationic polymer and at least one amino acid, together with the preparation comprising the at least one alkalizing agent and optionally at least one oxidation dye precursor and/or at least one direct dye, but separately from the oxidizing agent preparation comprising at least one peroxide compound, and to prepare the coloring or blonding agent according to the invention, or the preferred coloring or blonding agent according to the invention, just prior to starting the method according to the invention, or the preferred method according to the invention, by mixing the two components.

A further subject matter of the present invention is thus a method for oxidatively coloring and/or lightening keratin fibers, and in particular human hair, comprising the following method steps:

I. providing a composition (AB), comprising
    a) at least one polymer, which includes at least ten constitutional units of formula (I),

where
        X denotes nitrogen or oxygen, and
        $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, which are preferably selected from N and O, and/or optionally is substituted with at least one C1 to C6 alkyl group and/or with at least one functional group, and
        p=0 when X denotes oxygen, and p=1 when X denotes nitrogen,
    b) furthermore comprising at least one permanently cationic polymer,
    c) furthermore at least one amino acid,
    d) at least one alkalizing agent, selected from ammonium hydroxide, monoethanolamine and sodium silicates, and mixtures thereof,
    e) water, and
    f) optionally at least one oxidation dye precursor and/or at least one direct dye,
II. providing a composition (C), comprising
    g) at least one peroxide compound, which preferably is hydrogen peroxide,
III. mixing compositions (AB) and (C) with each other, immediately thereafter
IV. applying the mixture of (AB) and (C) to the keratin fibers, and in particular to the human hair, and
V. rinsing after an exposure time of 1 to 60 minutes,
VI. optionally further heat treatments, such as styling, conditioning and/or drying.

Mixing Ratios of Composition (AB) with Composition (C)

It has proven useful according to the invention if the weight ratio of composition (AB), which comprises the hair-protecting combination composed of at least one polymer, which includes at least ten constitutional units of formula (I), furthermore at least one permanently cationic polymer, at least one amino acid and water, in the alkalizing composition (B), comprising at least one alkalizing agent and optionally oxidation dye precursors and/or direct dyes, and composition (C), comprising at least one peroxide compound, is in the range of [weight of AB]/[weight of C] of 1:0.8 to 1:2.5, and preferably 1:1 to 1:2.

Coloring or lightening methods that are preferred according to the invention using the at least two aforementioned compositions (AB), and (C) are characterized in that the at least one polymer A including at least ten constitutional units of formula (I) is present in composition (AB) in a total amount of 0.8 to 10 wt. %, preferably 2 to 6 wt. %, and particularly preferably 3 to 5 wt. %, in each case based on the weight of composition (AB).

Coloring or lightening methods that are preferred according to the invention using the at least two aforementioned compositions (AB), and (C) are furthermore characterized in that the at least one permanently cationic polymer is present in composition (AB) in a total amount of 0.1 to 5 wt. %, preferably 0.2 to 3.0 wt. %, and particularly preferably 0.4 to 1.5 wt. %, in each case based on the weight of composition (AB).

Coloring or lightening methods that are preferred according to the invention using the at least two aforementioned compositions (AB), and (C) are furthermore characterized in that the at least one amino acid is present in composition (AB) in a total amount of 0.5 to 8 wt. %, preferably 0.9 to 5 wt. %, and particularly preferably 2 to 3 wt. %, in each case based on the weight of composition (AB).

Further coloring or lightening methods that are preferred according to the invention using the at least two aforementioned compositions (AB), and (C) are characterized in that a mixture of serine and at least one of the basic amino acids arginine, histidine or lysine is present in composition (AB) in a total amount of 0.5 to 8 wt. %, preferably 0.9 to 5 wt. %, and particularly preferably 2 to 3 wt. %, each based on the weight of composition (AB), wherein particularly preferably serine and at least one of the basic amino acids arginine, histidine or lysine are present in a molar ratio of serine to basic amino acids overall in the range of 1:1 to 50:1, and preferably 5:1 to 30:1.

Further coloring or lightening methods that are preferred according to the invention using the at least two aforementioned compositions (AB), and (C) are characterized in that composition (AB) comprises one or more compounds of above-mentioned formula (III) in a total amount of 0.002 to 2.5 wt. %, more preferably 0.02 to 2.0 wt. %, and particularly preferably 0.04 to 0.2 wt. %, in each case based on the weight of composition (AB).

Further coloring or lightening methods that are preferred according to the invention using the at least two aforementioned compositions (AB) and (C) are characterized in that composition (C) comprises 1.0 to 23.0 wt. %, more preferably 2.5 to 21.0 wt. %, particularly preferably 4.0 to 20.0 wt. %, and especially particularly preferably 5.0 to 18.0 wt. % hydrogen peroxide (calculated as 100% $H_2O_2$), in each case based on the total weight of composition (C).

Apart from the modified quantitative information cited above, what was said above with respect to the coloring and blonding agents according to the invention and the preferred coloring and blonding agents according to the invention applies, mutatis mutandis, to the method according to the invention for oxidatively coloring and/or lightening keratin fibers, and in particular human hair, using the at least two above-described compositions (AB) and (C), and the preferred embodiments thereof.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An oxidative coloring or blonding agent for keratin fibers, comprising:
    a) 0.9 to 3 wt % of at least one polymer A, which includes at least ten constitutional units of formula (I),

where
    X denotes nitrogen or oxygen, and
    $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, and/or optionally is substituted with at least one C1 to C6 alkyl group and/or with at least one functional group, and
    p=0 when X denotes oxygen, and p=1 when X denotes nitrogen,
    b) furthermore comprising at least two permanently cationic polymer selected from mixtures of at least one quaternized polysaccharide and at least one polymer comprising acrylamidopropyltrimethylammonium units,
    c) 0.5 wt % to 5 wt % of at least one amino acid,
    d) furthermore at least one alkalizing agent, selected from ammonium hydroxide, monoethanolamine and sodium silicates, and mixtures thereof,
    e) optionally at least one oxidation dye precursor and/or at least one direct dye,
    f) water, and
    g) at least one peroxide compound
    h) at least one compound of the general formula (III) is present in the coloring or blonding agent,

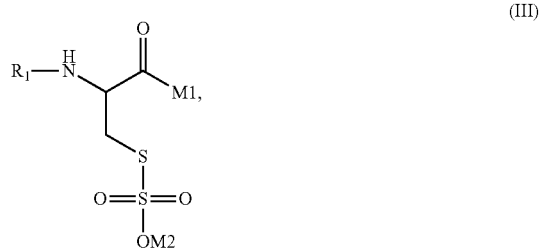

wherein

R1 denotes a hydrogen atom or a structural element of formula (IV)

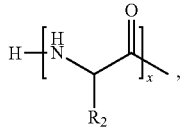

(IV)

wherein x denotes an integer from 1 to 100, the group R2 in each of the structural elements of formula (IV) can each be selected independently of a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group, M1 denotes the group —OM2 or a structural element of formula (V),

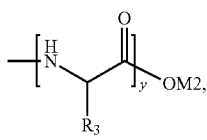

(V)

wherein y denotes an integer from 1 to 100, the group R3 in each of the structural elements of formula (V) can each be selected independently of a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group, M2 denotes a hydrogen atom, an equivalent of a monovalent or polyvalent cation, or an ammonium ion $(NH_4)^+$.

2. The coloring or blonding agent according to claim 1, wherein the at least one polymer A including at least ten constitutional units of formula (I) is selected from polymers that comprise 98 to 100 mol % of constitutional units of formula (Ia)

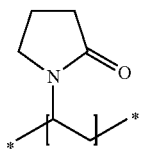

(Ia)

and have a degree of polymerization in the range of 40 to 1000, wherein the polymer A does not include any permanently ionic constitutional units.

3. The coloring or blonding agent according to claim 1, wherein the at least one polymer including at least ten constitutional units of formula (I) is present in a total amount of 1.5 to 2.3 wt. %, based on the weight of the coloring or blonding agent.

4. The coloring or blonding agent according to claim 1, wherein the at least one amino acid is selected from the group consisting of serine, arginine, histidine and lysine, and mixtures thereof.

5. The coloring or blonding agent according to claim 1, wherein the at least one amino acid is selected from the basic amino acids arginine, histidine and lysine.

6. The coloring or blonding agent according to claim 1, wherein the at least one amino acid includes serine and at least one of the basic amino acids arginine, histidine or lysine are present in a molar ratio of serine to basic amino acids overall in the range of 1:1 to 50:1.

7. The coloring or blonding agent according to claim 1, wherein the peroxide compound is hydrogen peroxide.

8. A method for oxidatively coloring and/or lighting keratin fibers, comprising applying a coloring or blonding agent according to claim 1 to keratin fibers, and rinsing off the coloring or blonding agent from the keratin fibers after an exposure time of 1 to 60 minutes.

9. A method for oxidatively coloring and/or lightening keratin fibers, comprising:

I. providing a composition (A), comprising a) at least one polymer, which includes at least ten constitutional units of formula (I),

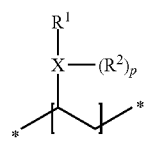

(I)

where

X denotes nitrogen or oxygen, and $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, and/or optionally is substituted with at least one C1 to C6 alkyl group and/or with at least one functional group, and p=0 when X denotes oxygen, and p=1 when X denotes nitrogen, b) furthermore comprising at least two permanently cationic polymer selected from mixtures of at least one quaternized polysaccharide and at least one polymer comprising acrylamidopropyltrimethylammonium units,
c) furthermore at least one amino acid,
d) water, and
e) at least one compound of the general formula (III) is present in the coloring or blonding agent,

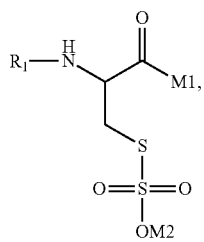
(III)

wherein
R1 denotes a hydrogen atom or a structural element of formula (IV)

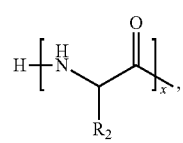
(IV)

wherein
x denotes an integer from 1 to 100,
the group R2 in each of the structural elements of formula (IV) can each be selected independently of a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group, M1 denotes the group —OM2 or a structural element of formula (V),

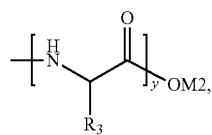
(V)

wherein
y denotes an integer from 1 to 100,
the group R3 in each of the structural elements of formula (V) can each be selected independently of a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group, M2 denotes a hydrogen atom, an equivalent of a monovalent or polyvalent cation, or an ammonium ion $(NH_4)^+$ II. providing a composition (B), comprising
  e) at least one alkalizing agent, selected from ammonium hydroxide, monoethanolamine and sodium silicates, and mixtures thereof,
  f) water, and
  g) optionally at least one oxidation dye precursor and/or at least one direct dye,
III. providing a composition (C), comprising
IV. at least one peroxide compound, mixing compositions (A), (B) and (C) with each other, immediately thereafter
V. applying the mixture of (A), (B) and (C) to the keratin fibers, and in particular to the human hair, and
VI. rinsing after an exposure time of 1 to 60 minutes,
VII. optionally further heat treatments.

10. The method according to claim 9, wherein the at least one not permanently ionically charged polymer is selected from polyvinylpyrrolidone, polyvinyl alcohol and mixtures thereof.

11. A method for oxidatively coloring and/or lightening keratin fibers, and in particular human hair, comprising the following method steps:
  I. providing a composition (AB), comprising
    a) 0.9 to 3 wt % of at least one polymer, which includes at least ten constitutional units of formula (I),

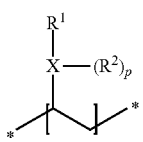
(I)

where
  X denotes nitrogen or oxygen, and
  $R^1$ and $R^2$, each independently of one another, denote hydrogen or a C2 to C10 acyl group, or $R^1$ and $R^2$ together form a five-membered or six-membered, saturated or unsaturated ring, which optionally includes further heteroatoms, and/or optionally is substituted with at least one C1 to C6 alkyl group and/or with at least one functional group, and
  p=0 when X denotes oxygen, and p=1 when X denotes nitrogen,
  b) furthermore comprising at least two permanently cationic polymer selected from mixtures of at least one quaternized polysaccharide and at least one polymer comprising acrylamidopropyltrimethylammonium units,
  c) 0.5 wt % to 5 wt % of at least one amino acid,
  d) at least one alkalizing agent, selected from ammonium hydroxide, monoethanolamine and sodium silicates, and mixtures thereof,
  e) water,
  f) optionally at least one oxidation dye precursor and/or at least one direct dye, and g) at least one compound of the general formula (III) is present in the coloring or blonding agent,

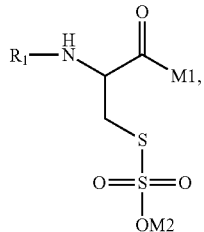
(III)

wherein
R1 denotes a hydrogen atom or a structural element of formula (IV)

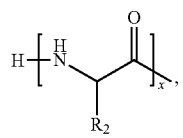
(IV)

wherein
x denotes an integer from 1 to 100,
the group R2 in each of the structural elements of formula (IV) can each be selected independently of a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group, M1 denotes the group —OM2 or a structural element of formula (V),

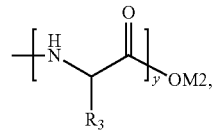
(V)

wherein
y denotes an integer from 1 to 100,
the group R3 in each of the structural elements of formula (V) can each be selected independently of a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulfanylmethyl group, a 2-(methylsulfanyl)ethyl group, a 1H-imidazole-4-ylmethyl group, a 1H-indole-3-ylmethyl group or a (sulfosulfanyl)methyl group, M2 denotes a hydrogen atom, an equivalent of a monovalent or polyvalent cation, or an ammonium ion $(NH_4)^+$ II. providing a composition (C), comprising
III. at least one peroxide compound,
IV. mixing compositions (AB) and (C) with each other, immediately thereafter
V. applying the mixture of (AB) and (C) to the keratin fibers, and in particular to the human hair, and
VI. rinsing after an exposure time of 1 to 60 minutes,
VII. optionally further heat treatments, such as styling, conditioning and/or drying.

12. The method according to claim 10, wherein the at least one not permanently ionically charged polymer is selected from polyvinylpyrrolidone, polyvinyl alcohol and mixtures thereof.

13. The method according to claim 10, wherein the at least one amino acid is selected from serine, arginine, histidine and lysine, and mixtures thereof.

* * * * *